US009321732B2

(12) United States Patent
Nising et al.

(10) Patent No.: US 9,321,732 B2
(45) Date of Patent: Apr. 26, 2016

(54) PHENYL(OXY/THIO)ALKANOL DERIVATIVES

(71) Applicant: Bayer Intellectual Property GmbH, Monheim (DE)

(72) Inventors: Carl Friedrich Nising, Langenfeld (DE); Klaus Kunz, Düsseldorf (DE); Jörg Nico Greul, Leichlingen (DE); Hendrick Helmke, Liederbach (DE); Gorka Peris, Köln (DE); Jürgen Benting, Leichlingen (DE); Peter Dahmen, Neuss (DE); Isolde Hauser-Hahn, Leverkusen (DE); Ines Heinemann, Hofheim (DE); Christian Paulitz, Liederbach am Taunus (DE); Dirk Schmutzler, Hattersheim (DE); Ulrike Wachendorff-Neumann, Neuwied (DE); Tomoki Tsuchiya, Düsseldorf (DE); Christoph Andreas Braun, Düsseldorf (DE); Ruth Meissner, Leverkusen (DE); Thomas Knobloch, Chatillon d'Azergues (FR)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/458,867

(22) Filed: Aug. 13, 2014

(65) Prior Publication Data

US 2014/0357649 A1 Dec. 4, 2014

Related U.S. Application Data

(63) Continuation of application No. 12/832,540, filed on Jul. 8, 2010, now Pat. No. 9,052,277.

(30) Foreign Application Priority Data

Jul. 8, 2009 (EP) .................................... 09164928

(51) Int. Cl.
| | | |
|---|---|---|
| *A01N 43/54* | (2006.01) | |
| *A01N 43/653* | (2006.01) | |
| *A01N 43/40* | (2006.01) | |
| *C07D 239/26* | (2006.01) | |
| *C07D 405/04* | (2006.01) | |
| *C07D 249/08* | (2006.01) | |
| *C07D 211/70* | (2006.01) | |
| *C07D 213/30* | (2006.01) | |
| *C07D 213/32* | (2006.01) | |
| *C07D 213/34* | (2006.01) | |

(52) U.S. Cl.
CPC .............. *C07D 239/26* (2013.01); *A01N 43/40* (2013.01); *A01N 43/54* (2013.01); *A01N 43/653* (2013.01); *C07D 213/30* (2013.01); *C07D 213/32* (2013.01); *C07D 213/34* (2013.01); *C07D 249/08* (2013.01); *C07D 405/04* (2013.01)

(58) Field of Classification Search
CPC .. C07D 239/26; C07D 405/04; C07D 249/08; C07D 211/70; A01N 43/54; A01N 43/653; A01N 43/40
USPC .................. 514/256, 383, 277, 336; 544/335; 546/281.7, 344; 548/268.6
See application file for complete search history.

(56) References Cited

U.S. PATENT DOCUMENTS

| | | | |
|---|---|---|---|
| 4,438,122 | A | 3/1984 | Holmwood et al. |
| 4,518,600 | A | 5/1985 | Holmwood et al. |
| 4,525,204 | A | 6/1985 | Holmwood et al. |
| 4,584,373 | A | 4/1986 | Holmwood et al. |
| 4,677,128 | A | 6/1987 | Place et al. |
| 4,734,126 | A | 3/1988 | Holmwood et al. |
| 4,797,499 | A | 1/1989 | Holmwood et al. |
| 4,904,296 | A | 2/1990 | Holmwood et al. |
| 4,925,482 | A | 5/1990 | Stroech et al. |
| 4,938,791 | A | 7/1990 | Stroech et al. |
| 4,960,456 | A | 10/1990 | Holmwood et al. |
| 4,983,208 | A | 1/1991 | Stroech et al. |
| 5,079,374 | A | 1/1992 | Stroech et al. |

(Continued)

FOREIGN PATENT DOCUMENTS

| | | |
|---|---|---|
| DE | 27 42 175 A1 | 3/1979 |
| DE | 39 05 317 A1 | 8/1990 |
| DE | 42 29 643 A1 | 3/1994 |

(Continued)

OTHER PUBLICATIONS

Unverified English language translation of German Patent Application No. DE 24 42 175 A1, European Patent Office, espacenet database—Worldwide, published Mar. 29, 1979.

(Continued)

*Primary Examiner* — James O Wilson
*Assistant Examiner* — Ebenezer O Sackey
(74) *Attorney, Agent, or Firm* — Sterne, Kessler, Goldstein, Fox P.L.L.C.

(57) ABSTRACT

The present invention relates to novel phenyl(oxy/thio)alkanol derivatives, to processes for preparing these compounds, to compositions comprising these compounds and to their use as biologically active compounds, in particular for controlling harmful microorganisms in crop protection and in the protection of materials and as plant growth regulators.

6 Claims, No Drawings

(56) References Cited

U.S. PATENT DOCUMENTS

| | | | |
|---|---|---|---|
| 5,356,899 | A | 10/1994 | Elbe et al. |
| 2011/0059990 | A1 | 3/2011 | Nising et al. |

FOREIGN PATENT DOCUMENTS

| | | | |
|---|---|---|---|
| EP | 0 001 399 | A1 | 4/1979 |
| EP | 0 028 755 | A1 | 5/1981 |
| EP | 0 040 345 | A1 | 11/1981 |
| EP | 0 061 835 | A1 | 10/1982 |
| EP | 0 084 834 | A2 | 8/1983 |
| EP | 0 086 173 | A1 | 8/1983 |
| EP | 0 131 867 | A2 | 1/1985 |
| EP | 0 297 383 | A2 | 1/1989 |
| EP | 0 298 332 | A1 | 1/1989 |
| EP | 0 304 171 | B1 | 1/1993 |
| EP | 1 283 209 | A1 | 2/2003 |
| IL | 67677 | A | 2/1986 |

OTHER PUBLICATIONS

Office Action mailed Sep. 28, 2012, in U.S. Appl. No. 12/832,558, Nising et al., filed Jul. 8, 2010.
International Search Report for International Application No. PCT/EP2010/003908, European Patent Office, Rijswijk, Netherlands, mailed on Oct. 13, 2010.
Office Action dated Apr. 2, 2013 from the US Patent and Trademark Office Re.: U.S. Appl. No. 12/832,558, Nising et al., filed Jul. 8, 2010.
Office Action dated Jun. 17, 2014 from the US Patent and Trademark Office Re.: U.S. Appl. No. 12/832,558, Nising et al., filed Jul. 8, 2010.
STN Database, Chemical Accession No. 1152622-42-8, "2-Butanont, 1-[(3-bromophenyl)thio]-3-3-dimethyl-," entered in STN on Jun. 5, 2009, accessed on Jan. 14, 2015.
STN Database, Chemical Accession No. 379704-91-3, "2-Butanone, 1-[(4-bromophenyl)thio]-3,3-dimethyl-," entered in STN on Dec. 31, 2001, accessed on Jan. 13, 2015.
Office Action mailed Mar. 17, 2015 in U.S. Appl. No. 12/832,558, inventors Nising et al., filed Jul. 8, 2010.

PHENYL(OXY/THIO)ALKANOL DERIVATIVES

This application is a continuation of U.S. application Ser. No. 12/832,540, filed on Jul. 8, 2010, which claims priority to EP Application No. 09164928.5, filed Jul. 8, 2009. The disclosure of which are incorporated by reference in its entirety.

The present invention relates to novel phenyl(oxy/thio) alkanol derivatives, to processes for preparing these compounds, to compositions comprising these compounds and to their use as biologically active compounds, in particular for controlling harmful microorganisms in crop protection and in the protection of materials and as plant growth regulators.

It is already known that certain phenyl(oxy/thio)alkanol derivatives can be used in crop protection as fungicides and/or growth regulators (cf. DE-A 39 05 317, JP-A 58-124772, EP-A 0 298 332, EP-A 0 028 755, EP-A 0 061 835, EP-A 0 040 345, EP-A 0 001 399, EP-A 0 793 657 and EP-A 0 594 963).

Since the ecological and economical demands made on modern active compounds, for example fungicides, are increasing constantly, for example with respect to activity spectrum, toxicity, selectivity, application rate, formation of residues and favourable manufacture, and there can furthermore be problems, for example, with resistances, there is a constant need to develop novel fungicides which, at least in some areas, have advantages over the known ones.

This invention, accordingly, provides novel phenyl(oxy/thio)alkanol derivatives of the formula (I)

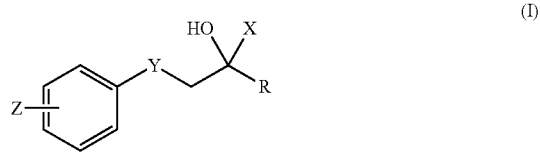

in which
X represents 5-pyrimidinyl, 1H-1,2,4-triazol-1-ylmethyl, 3-pyridinyl, 1H-1,3-imidazol-1-ylmethyl or 2,4-dihydro-3H-1,2,4-triazole-3-thion-1-ylmethyl,
Y represents O, S, SO, $SO_2$ or $CH_2$,
Z represents bromine or iodine,
R represents tert-butyl, isopropyl, 1-halocyclopropyl, 1-($C_1$-$C_4$-alkyl)cyclopropyl, 1-($C_1$-$C_4$-alkoxy)cyclopropyl or 1-($C_1$-$C_4$-alkylthio)cyclopropyl,
and the agrochemically active salts thereof,
except for the compounds
1-(4-bromophenoxy)-3,3-dimethyl-2-(pyridin-3-yl)butan-2-ol
1-(4-bromophenylthio)-3,3-dimethyl-2-(pyridin-3-yl)butan-2-ol
1-(4-bromophenylthio)-3-methyl-2-(pyridin-3-yl)butan-2-ol
2-(4-bromophenoxy)-1-(1-chlorocyclopropyl)-1-(pyridin-3-yl)ethanol
1-(4-bromophenoxy)-3,3-dimethyl-2-(1H-1,2,4-triazol-1-ylmethyl)butan-2-ol
1-(4-bromophenyl)-4,4-dimethyl-3-(1H-1,2,4-triazol-1-ylmethyl)pentan-3-ol
4-(4-bromophenyl)-2-(1-methylcyclopropyl)-1-(1H-1,2,4-triazol-1-yl)butan-2-ol
4-(4-bromophenyl)-2-(1-chlorocyclopropyl)-1-(1H-1,2,4-triazol-1-yl)butan-2-ol.

The salts obtainable in this manner also have fungicidal and/or plant growth regulatory properties.

The formula (I) provides a general definition of the phenyl (oxy/thio)alkanol derivatives which can be used according to the invention. Preferred radical definitions for the formulae shown above and below are given below. These definitions apply to the end products of the formula (I) and likewise to all intermediates (see also below under "Illustration of the processes and intermediates").

X preferably represents 5-pyrimidinyl, 1H-1,2,4-triazol-1-ylmethyl, 3-pyridinyl or 2,4-dihydro-3H-1,2,4-triazole-3-thion-1-ylmethyl.
X particularly preferably represents 5-pyrimidinyl.
X also particularly preferably represents 1H-1,2,4-triazol-1-ylmethyl.
X also particularly preferably represents 2,4-dihydro-3H-1,2,4-triazole-3-thion-1-ylmethyl.
X very particularly preferably represents 5-pyrimidinyl.
X also very particularly preferably represents 1H-1,2,4-triazol-1-ylmethyl.
Y preferably represents O, S or $CH_2$.
Y particularly preferably represents O or $CH_2$.
Y very particularly preferably represents O.
Z preferably represents bromine.
Z also preferably represents iodine.
Z particularly preferably represents bromine which is located in position 4.
Z also particularly preferably represents bromine which is located in position 3.
Z also particularly preferably represents bromine which is located in position 2.
Z also particularly preferably represents iodine which is located in position 4.
Z also particularly preferably represents iodine which is located in position 3.
Z also particularly preferably represents iodine which is located in position 2.
R preferably represents tert-butyl, isopropyl, 1-chlorocyclopropyl, 1-fluorocyclopropyl, 1-methylcyclopropyl, 1-methoxycyclopropyl or 1-methylthiocyclopropyl.
R particularly preferably represents tert-butyl, isopropyl, 1-chlorocyclopropyl, 1-fluorocyclopropyl or 1-methylcyclopropyl.
R very particularly preferably represents tert-butyl.
R also very particularly preferably represents isopropyl.
R also very particularly preferably represents 1-chlorocyclopropyl.
R also very particularly preferably represents 1-fluorocyclopropyl.
R also very particularly preferably represents 1-methylcyclopropyl.

A further embodiment of the present invention relates to compounds of the formula (I-a)

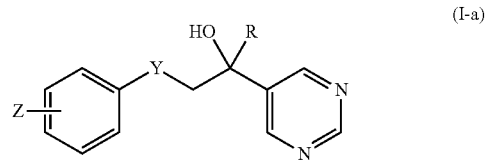

in which Y, Z and R have the meanings given above.
A further embodiment of the present invention relates to compounds of the formula (I-b)

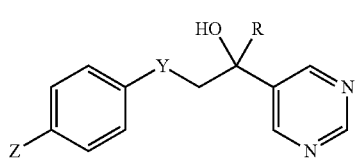

in which Y, Z and R have the meanings given above.

A further embodiment of the present invention relates to compounds of the formula (I-c)

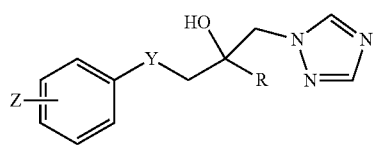

in which Y, Z and R have the meanings given above.

In this formula (I-c), Z preferably represents iodine.

A further embodiment of the present invention relates to compounds of the formula (I-d)

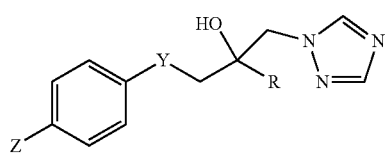

in which Y, Z and R have the meanings given above.

In this formula (I-d), Z preferably represents iodine.

A further embodiment of the present invention relates to compounds of the formula (I-e)

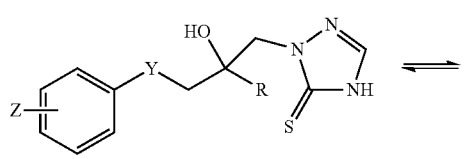 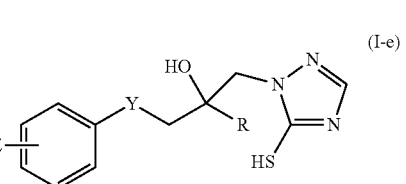

in which Y, Z and R have the meanings given above.

A further embodiment of the present invention relates to compounds of the formula (I-f)

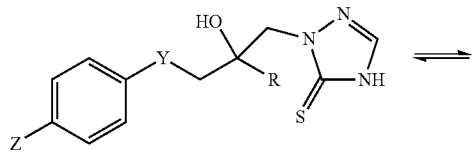 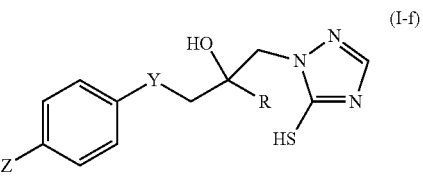

in which Y, Z and R have the meanings given above.

A further embodiment of the present invention are compounds of the formula (I) in which Z represents bromine and R represents tert-butyl.

A further embodiment of the present invention are compounds of the formula (I) in which Z represents bromine and R represents isopropyl.

A further embodiment of the present invention are compounds of the formula (I) in which Z represents bromine and R represents 1-chlorocyclopropyl.

A further embodiment of the present invention are compounds of the formula (I) in which Z represents bromine and R represents 1-fluorocyclopropyl.

A further embodiment of the present invention are compounds of the formula (I) in which Z represents bromine and R represents 1-methylcyclopropyl.

A further embodiment of the present invention are compounds of the formula (I) in which Z represents iodine and R represents tert-butyl.

A further embodiment of the present invention are compounds of the formula (I) in which Z represents iodine and R represents isopropyl.

A further embodiment of the present invention are compounds of the formula (I) in which Z represents iodine and R represents 1-chlorocyclopropyl.

A further embodiment of the present invention are compounds of the formula (I) in which Z represents iodine and R represents 1-fluorocyclopropyl.

A further embodiment of the present invention are compounds of the formula (I) in which Z represents iodine and R represents 1-methylcyclopropyl.

A further embodiment of the present invention are compounds of the formula (I) in which Z represents bromine, R represents tert-butyl and X represents 5-pyrimidinyl.

A further embodiment of the present invention are compounds of the formula (I) in which Z represents bromine, R represents tert-butyl and X represents 1H-1,2,4-triazol-1-yl-methyl.

A further embodiment of the present invention are compounds of the formula (I) in which Z represents bromine, R represents tert-butyl and X represents 3-pyridinyl.

A further embodiment of the present invention are compounds of the formula (I) in which Z represents bromine, R represents tert-butyl and X represents 2,4-dihydro-3H-1,2,4-triazole-3-thion-1-ylmethyl.

A further embodiment of the present invention are compounds of the formula (I) in which Z represents bromine, R represents isopropyl and X represents 5-pyrimidinyl.

A further embodiment of the present invention are compounds of the formula (I) in which Z represents bromine, R represents isopropyl and X represents 1H-1,2,4-triazol-1-ylmethyl.

A further embodiment of the present invention are compounds of the formula (I) in which Z represents bromine, R represents isopropyl and X represents 3-pyridinyl.

A further embodiment of the present invention are compounds of the formula (I) in which Z represents bromine, R represents isopropyl and X represents 2,4-dihydro-3H-1,2,4-triazole-3-thion-1-ylmethyl.

A further embodiment of the present invention are compounds of the formula (I) in which Z represents bromine, R represents 1-chlorocyclopropyl and X represents 5-pyrimidinyl.

A further embodiment of the present invention are compounds of the formula (I) in which Z represents bromine, R represents 1-chlorocyclopropyl and X represents 1H-1,2,4-triazol-1-ylmethyl.

A further embodiment of the present invention are compounds of the formula (I) in which Z represents bromine, R represents 1-chlorocyclopropyl and X represents 3-pyridinyl.

A further embodiment of the present invention are compounds of the formula (I) in which Z represents bromine, R represents 1-chlorocyclopropyl and X represents 2,4-dihydro-3H-1,2,4-triazole-3-thion-1-ylmethyl.

A further embodiment of the present invention are compounds of the formula (I) in which Z represents bromine, R represents 1-fluorocyclopropyl and X represents 5-pyrimidinyl.

A further embodiment of the present invention are compounds of the formula (I) in which Z represents bromine, R represents 1-fluorocyclopropyl and X represents 1H-1,2,4-triazol-1-ylmethyl.

A further embodiment of the present invention are compounds of the formula (I) in which Z represents bromine, R represents 1-fluorocyclopropyl and X represents 3-pyridinyl.

A further embodiment of the present invention are compounds of the formula (I) in which Z represents bromine, R represents 1-fluorocyclopropyl and X represents 2,4-dihydro-3H-1,2,4-triazole-3-thion-1-ylmethyl.

A further embodiment of the present invention are compounds of the formula (I) in which Z represents iodine, R represents tert-butyl and X represents 5-pyrimidinyl.

A further embodiment of the present invention are compounds of the formula (I) in which Z represents iodine, R represents tert-butyl and X represents 1H-1,2,4-triazol-1-ylmethyl.

A further embodiment of the present invention are compounds of the formula (I) in which Z represents iodine, R represents tert-butyl and X represents 3-pyridinyl.

A further embodiment of the present invention are compounds of the formula (I) in which Z represents iodine, R represents tert-butyl and X represents 2,4-dihydro-3H-1,2,4-triazole-3-thion-1-ylmethyl.

A further embodiment of the present invention are compounds of the formula (I) in which Z represents iodine, R represents isopropyl and X represents 5-pyrimidinyl.

A further embodiment of the present invention are compounds of the formula (I) in which Z represents iodine, R represents isopropyl and X represents 1H-1,2,4-triazol-1-ylmethyl.

A further embodiment of the present invention are compounds of the formula (I) in which Z represents iodine, R represents isopropyl and X represents 3-pyridinyl.

A further embodiment of the present invention are compounds of the formula (I) in which Z represents iodine, R represents isopropyl and X represents 2,4-dihydro-3H-1,2,4-triazole-3-thion-1-ylmethyl.

A further embodiment of the present invention are compounds of the formula (I) in which Z represents iodine, R represents 1-chlorocyclopropyl and X represents 5-pyrimidinyl.

A further embodiment of the present invention are compounds of the formula (I) in which Z represents iodine, R represents 1-chlorocyclopropyl and X represents 1H-1,2,4-triazol-1-ylmethyl.

A further embodiment of the present invention are compounds of the formula (I) in which Z represents iodine, R represents 1-chlorocyclopropyl and X represents 3-pyridinyl.

A further embodiment of the present invention are compounds of the formula (I) in which Z represents iodine, R represents 1-chlorocyclopropyl and X represents 2,4-dihydro-3H-1,2,4-triazole-3-thion-1-ylmethyl.

A further embodiment of the present invention are compounds of the formula (I) in which Z represents iodine, R represents 1-fluorocyclopropyl and X represents 5-pyrimidinyl.

A further embodiment of the present invention are compounds of the formula (I) in which Z represents iodine, R represents 1-fluorocyclopropyl and X represents 1H-1,2,4-triazol-1-ylmethyl.

A further embodiment of the present invention are compounds of the formula (I) in which Z represents iodine, R represents 1-fluorocyclopropyl and X represents 3-pyridinyl.

A further embodiment of the present invention are compounds of the formula (I) in which Z represents iodine, R represents 1-fluorocyclopropyl and X represents 2,4-dihydro-3H-1,2,4-triazole-3-thion-1-ylmethyl.

A further embodiment of the present invention are compounds of the formula (I) in which Z represents bromine, R represents 1-methylcyclopropyl and X represents 5-pyrimidinyl.

A further embodiment of the present invention are compounds of the formula (I) in which Z represents bromine, R represents 1-methylcyclopropyl and X represents 1H-1,2,4-triazol-1-ylmethyl.

A further embodiment of the present invention are compounds of the formula (I) in which Z represents bromine, R represents 1-methylcyclopropyl and X represents 3-pyridinyl.

A further embodiment of the present invention are compounds of the formula (I) in which Z represents bromine, R represents 1-methylcyclopropyl and X represents 2,4-dihydro-3H-1,2,4-triazole-3-thion-1-ylmethyl.

The radical definitions and explanations stated above in general or stated in preferred ranges can, however, also be combined as desired with one another, that is to say between the respective ranges and preferred ranges. They apply both to the end products and, correspondingly, to precursors and intermediates. Moreover, individual definitions may not apply.

Preference is given to compounds of the formula (I) in which all radicals have the preferred meanings mentioned above.

Particular preference is given to compounds of the formula (I) in which all radicals have the particularly preferred meanings mentioned above.

Illustration of the Processes and Intermediates

The phenyl(oxy/thio)alkanol derivatives of the formula (I) can be prepared by various routes. Initially, the feasable processes are shown schematically below. Unless indicated otherwise, the radicals given have the meanings given above.

Scheme 1:
Process A - Preparation of phenyl(oxy/thio)alkanol derivatives of the formula (I-g) ($X^1$ = 1H-1,2,4-triazol-1-ylmethyl, 1H-1,3-imidazol-1-ylmethyl)

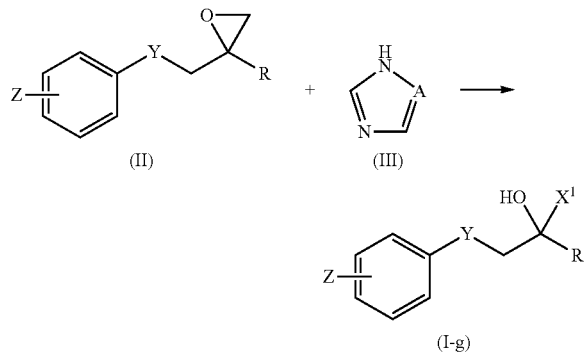

A represents CH or N.

Scheme 2:
Process B - Preparation of phenyl(oxy/thio)alkanol derivatives of the formula (I-h) ($X^2$ = 1H-1,2,4-triazol-1-ylmethyl, 1H-1,3-imidazol-1-ylmethyl, 5-pyrimidinyl or 3-pyridinyl)

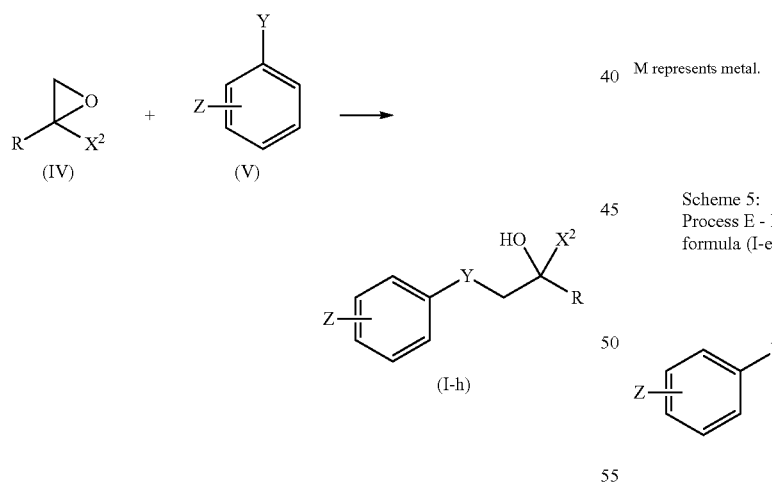

Scheme 3:
Process C - Preparation of phenyl(oxy/thio)alkanol derivatives of the formula (I-i) ($X^3$ = 5-pyrimidinyl or 3-pyridinyl)

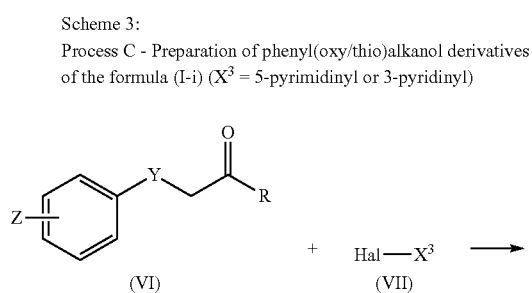

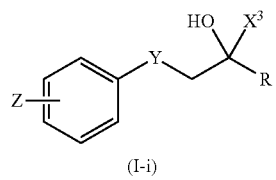

Hal represents halogen.

Scheme 4:
Process D - Preparation of phenyl(oxy/thio)alkanol derivatives of the formula (I-k) ($X^4$ = 5-pyrimidinyl or 3-pyridinyl)

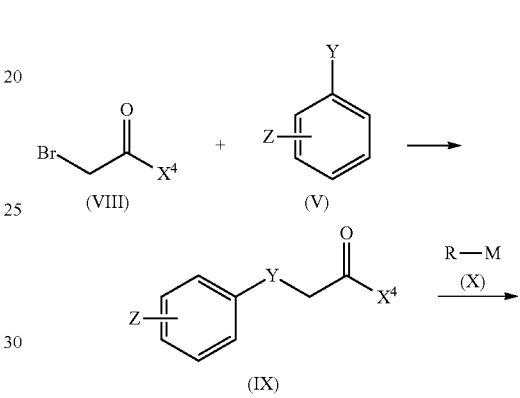

M represents metal.

Scheme 5:
Process E - Preparation of phenyl(oxy/thio)alkanol derivatives of the formula (I-e)

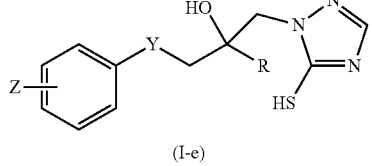

Preferred radical definitions for the formulae and schemes shown above and below have already been given above. These definitions apply not only to the end products of the formula (I) but likewise to all intermediates.

Process A

The oxirane derivatives of the formula (II) required as starting materials for carrying out the process A according to the invention are novel, except for the compound 2-[2-(4-bromophenyl)ethyl]-2-(1-methylcyclopropyl)oxirane. They can be prepared by known processes from the phenyloxy (thio)ketones of the formula (VI) (cf. EP-A 0 040 345).

The 1,2,4-triazole and the 1,3-imidazole of the formula (III) are known.

The process A according to the invention is carried out in the presence of a diluent and, if appropriate, in the presence of a base. If appropriate, an acid or a metal salt is then added to the compound of the formula (I-g) obtained (see below).

Suitable diluents for the reaction according to the invention are all organic solvents which are inert. These preferably include alcohols, such as, for example, ethanol and methoxyethanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Suitable bases for the reaction according to the invention are all organic and inorganic bases which can customarily be used. These preferably include alkali metal carbonates, such as, for example, sodium carbonate or potassium carbonate; alkali metal hydroxides, such as, for example, sodium hydroxide; alkali metal alkoxides, such as, for example, sodium methoxide and potassium methoxide and sodium ethoxide and potassium ethoxide; alkali metal hydrides, such as, for example, sodium hydride; and also lower tertiary alkylamines, cycloalkylamines and aralkylamines, such as, in particular, triethylamine.

When carrying out the process according to the invention, the reaction temperatures can be varied within a relatively wide range. In general, the process is carried out at temperatures between 0° C. and 200° C., preferably between 60° C. and 150° C.

If appropriate, the reaction according to the invention can be carried out under elevated pressure. In general, the reaction is carried out between 1 and 50 bar, preferably between 1 and 25 bar.

When carrying out the process A according to the invention, preferably from 1 to 2 mol of 1,2,4-triazole or 1,3-imidazole of the formula (III) and, if appropriate, from 1 to 2 mol of base are employed per mole of oxirane of the general formula (II). The isolation of the end products is carried out in a generally customary manner.

Process B

Some of the oxirane derivatives of the formula (IV) required as starting materials for carrying out the process B according to the invention are novel. They can be prepared by known processes from the corresponding triazolylketones (cf. DE-A 31 11 238, EP-A 0 157 712).

Oxirane derivatives of the formula (IV-a)

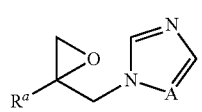

(IV-a)

in which
R¹ represents isopropyl, 1-halocyclopropyl, 1-($C_1$-$C_4$-alkyl) cyclopropyl, 1-($C_1$-$C_4$-alkoxy)cyclopropyl or 1-($C_1$-$C_4$-alkylthio)cyclopropyl, A represents CH or N are novel.
$R^a$ preferably represents isopropyl, 1-chlorocyclopropyl, 1-methylcyclopropyl, 1-methoxycyclopropyl or 1-methylthiocyclopropyl.
$R^a$ particularly preferably represents isopropyl, 1-chlorocyclopropyl or 1-methylcyclopropyl.
$R^a$ very particularly preferably represents isopropyl.

Oxirane derivatives of the formula (IV-b)

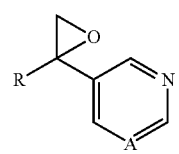

(IV-b)

in which
R has the meanings given above and
A represents CH or N,
where R does not represent tert-butyl if A represents CH are likewise novel.
R preferably particularly preferably and very particularly preferably has the meanings given above, where in each case R does not represent tert-butyl if A represents CH.

The (thio)phenols of the formula (V) are known.

The process B according to the invention is carried out in the presence of a diluent and, if appropriate, in the presence of a base. If appropriate, an acid or a metal salt is then added to the compound of the formula (I-h) obtained (see below).

Suitable diluents for the reaction according to the invention are all organic solvents which are inert. These preferably include alcohols, such as, for example, ethanol and methoxyethanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Suitable bases for the reaction according to the invention are all organic and inorganic bases which can customarily be used. These preferably include alkali metal carbonates, such as, for example, sodium carbonate or potassium carbonate; alkali metal hydroxides, such as, for example, sodium hydroxide; alkali metal alkoxides, such as, for example, sodium methoxide and potassium methoxide and sodium ethoxide and potassium ethoxide; alkali metal hydrides, such as, for example, sodium hydride; and also lower tertiary alkylamines, cycloalkylamines and aralkylamines, such as, in particular, triethylamine. Particular preference is given to using sodium hydride.

When carrying out the process according to the invention, the reaction temperatures can be varied within a relatively wide range. In general, the process is carried out at temperatures between 0° C. and 200° C., preferably between 60° C. and 150° C.

If appropriate, the reaction according to the invention can be carried out under elevated pressure. In general, the reaction is carried out between 1 and 50 bar, preferably between 1 and 25 bar.

When carrying out the process B according to the invention, preferably from 1 to 2 mol of (thio)phenol of the formula (V) and, if appropriate, from 1 to 2 mol of base are employed per mole of oxirane of the general formula (IV). The isolation of the end products is carried out in a generally customary manner.

Process C

The phenyl(oxy/thio)ketones of the formula (VI) where Y does not represent O or $CH_2$ if Z represents bromine required as starting materials for carrying out the process C according to the invention are novel. They can be prepared in a known manner (cf. EP-A 0 040 345, EP-A 0 001 399).

The halides of the formula (VII) are known. In formula (VII), Hal is preferably chlorine or bromine.

The process C according to the invention is carried out in the presence of a diluent and in the presence of an organic alkali metal compound. If appropriate, an acid or a metal salt is then added to the compound of the formula (I-i) obtained (see below).

Preferred diluents for the reaction according to the invention are inert organic solvents. These preferably include those having a low freezing point, such as, in particular, ethers, such as diethyl ether or tetrahydrofuran. Preference is given to working with mixtures of these two ethers.

Preferred organic alkali metal compounds used for the reaction according to the invention are alkali metal alkyls, such as, in particular, n-butyllithium; however, it is also possible to use alkali metal aryls, such as phenyllithium.

In the process according to the invention, the reaction temperatures can be varied within a certain range. In general, the process is carried out at temperatures between −150° C. and −50° C., preferably between −120° and −80° C.

The reaction according to the invention is preferably carried out under inert gas such as, in particular, nitrogen or argon.

When carrying out the process according to the invention, the phenyloxy(thio)ketones of the formula (VI) and the halides of the formula (VII) are employed in approximately equimolar amounts; however, it is possible to be above or below this ratio by up to about 20 mol percent. The organic alkali metal compound is advantageously employed in an excess of from 5 to 75 mol percent, preferably from 10 to 50 mol percent.

Here, the organic alkali metal compound may initially be allowed to react with the halide of the formula (VII), and the keto compound of the formula (VI) may then be added; however, it is also possible to initially charge the keto compound and the halide and then to add the organic alkali metal compound at low temperature (for example at from −100° C. to −130° C.). The isolation of the compounds of the formula (I-b) is carried out by hydrolyzing, with water, the alkali metal alkoxide (for example lithium alkoxide) initially formed in the reaction. Further work-up is then carried out in a customary manner.

Process D

The bromides of the formula (VIII) are known. The (thio)phenols of the formula (V) are likewise known.

The phenyl(oxy/thio)ketones of the formula (IX) where Z does not represent bromine if $X^4$ represents 3-pyridinyl occurring as intermediates for carrying out the process D according to the invention are novel. They can be prepared in a known manner (cf. JP-A 62-084061, WO 01/87878).

The organometal compounds of the formula (X) are known, where M in formula (X) preferably represents lithium or magnesium.

The process D (step 1) according to the invention is carried out in the presence of a diluent and, if appropriate, in the presence of a base. Suitable diluents for the reaction according to the invention are all organic solvents which are inert. These preferably include alcohols, such as, for example, ethanol and methoxyethanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Suitable bases for the reaction according to the invention are all organic and inorganic bases which can customarily be used. These preferably include alkali metal carbonates, such as, for example, sodium carbonate or potassium carbonate; alkali metal hydroxides, such as, for example, sodium hydroxide; alkali metal alkoxides, such as, for example, sodium methoxide and potassium methoxide and sodium ethoxide and potassium ethoxide; alkali metal hydrides, such as, for example, sodium hydride; and also lower tertiary alkylamines, cycloalkylamines and aralkylamines, such as, in particular, triethylamine.

When carrying out the process according to the invention, the reaction temperatures can be varied within a relatively wide range. In general, the process is carried out at temperatures between 0° C. and 200° C., preferably between 20° C. and 100° C.

If appropriate, the reaction according to the invention can be carried out under elevated pressure. In general, the reaction is carried out between 1 and 50 bar, preferably between 1 and 25 bar.

When carrying out the process D (step 1) according to the invention, preferably from 1 to 2 mol of (thio)phenol of the formula (V) and, if appropriate, from 1 to 3 mol of base are employed per mole of bromoketone of the general formula (VIII). The isolation of the end products is carried out in a generally customary manner.

The process D (step 2) according to the invention is carried out in the presence of a diluent and in the presence of an organic alkali metal compound. If appropriate, an acid or a metal salt is then added to the compound of the formula (I-k) obtained (see below).

Preferred diluents for the conversion according to the invention of compounds of the formula (IX) into compounds of the formula (I-k) are inert organic solvents. These include in particular ethers, such as diethyl ether or tetrahydrofuran. Preferred organic alkali metal compounds used for the reaction according to the invention are alkaline earth metal alkyls, such as, in particular, t-butylmagnesium chloride; however, it is also possible to use alkali metal alkyls, such as t-butyllithium.

In the process according to the invention, the reaction temperatures can be varied within a certain range. In general, the process is carried out at temperatures between −100° C. and +20° C., preferably between −78° C. and 0° C.

The reaction according to the invention is preferably carried out under inert gas such as, in particular, nitrogen or argon.

When carrying out the process according to the invention, the ketones of the formula (IX) and the organometal compounds of the formula (X) are employed in approximately equimolar amounts; however, it is possible to be above or below this ratio by up to about 20 mol percent. The organometal compound is advantageously employed in an excess of from 5 to 75 mol percent, preferably from 10 to 50 mol percent.

Here, the ketone (IX) may be initially charged, and the organometal compound of the formula (X) may then be added at a suitable temperature (for example 0° C.). The isolation of the compounds of the formula (I-k) is carried out by hydrolyzing, with water, the metal alkoxide (for example magnesium alkoxide) initially formed in the reaction. Further work-up is then carried out in a customary manner.

Process E

The conversion of the phenyl(oxy/thio)alkanol derivatives of the formula (I-c) into phenyl(oxy/thio)alkanol derivatives of the formula (I-e) can be carried out by two different routes (cf. EP-A 0 793 657).

Phenyl(oxy/thio)alkanol derivatives of the formula (I-c) are either (α) reacted successively with strong bases and sulphur in the presence of a diluent and then hydrolyzed with water, if appropriate in the presence of an acid, or (β) reacted with sulphur in the presence of a high-boiling diluent and then, if required, treated with water and, if required, with acid.

Suitable bases for carrying out the process E, variant (α), according to the invention are all strong alkali metal bases customary for such reactions. Preference is given to using n-butyllithium, lithium diisopropylamide, sodium hydride, sodium amide and also potassium tert-butoxide in a mixture with tetramethylethylenediamine (=TMEDA).

Suitable diluents for carrying out the process E, variant (α), according to the invention are all inert organic solvents customary for such reactions. Preference is given to using ethers, such as tetrahydrofuran, dioxane, diethyl ether and 1,2-dimethoxyethane, furthermore liquid ammonia or else strongly polar solvents, such as dimethyl sulphoxide.

Sulphur is preferably employed in the form of a powder. When carrying out the process E, variant (α), according to the invention, water, if appropriate in the presence of an acid, is used for carrying out the hydrolysis. Suitable acids are all inorganic or organic acids customary for such reactions. Preference is given to using acetic acid, dilute sulphuric acid and dilute hydrochloric acid. However, it is also possible to carry out the hydrolysis with aqueous ammonium chloride solution.

When carrying out the variant (α), the reaction temperatures may be varied within a certain range. In general, the variant is carried out at temperatures between −70° C. and +20° C., preferably between −70° C. and 0° C.

The process E according to the invention is generally carried out under atmospheric pressure. However, it is also possible to operate under elevated or reduced pressure. Thus, when carrying out variant (α), it is possible in particular to operate under elevated pressure.

When carrying out the process E according to the invention according to variant (α), in general from 2 to 3 equivalents, preferably from 2.0 to 2.5 equivalents, of strong base and subsequently an equivalent amount or else an excess of sulphur are employed per mole of phenyl(oxy/thio)alkanol derivatives of the formula (I-c). The reaction may be carried out under an atmosphere of protective gas, for example under nitrogen or argon. Work-up is carried out by customary methods.

Suitable diluents for carrying out the process E, variant (β), according to the invention are all high-boiling organic solvents customary for such reactions. Preference is given to using amides, such as dimethylformamide and dimethylacetamide, moreover heterocyclic compounds, such as N-methylpyrrolidone, and also ethers, such as diphenyl ether.

When carrying out the process E according to the invention according to variant (β), sulphur is also generally employed in the form of a powder. After the reaction, treatment with water and, if appropriate, acid may optionally be carried out. This takes place like the hydrolysis when carrying out variant (α).

When carrying out the process E, variant (β), according to the invention, the reaction temperatures can likewise be varied within a relatively wide range. In general, the variant is carried out at temperatures between 150° C. and 300° C., preferably between 180° C. and 250° C.

When carrying out the process E according to the invention according to variant (β), in general from 1 to 5 mol, preferably from 1.5 to 3 mol, of sulphur are employed per mole of phenyl(oxy/thio)alkanol derivatives of the formula (I-c). Work-up is carried out by customary methods.

The compounds of the general formula (I) which can be obtained by the processes A to E according to the invention can be converted into acid addition salts or metal salt complexes.

Suitable for producing physiologically acceptable acid addition salts of the compounds of the general formula (I) are preferably the following acids: hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid, lactic acid and also sulphonic acids, such as, for example, p-toluenesulphonic acid and 1,5-naphthalenedisulphonic acid.

The acid addition salts of the compounds of the general formula (I) can be obtained in a simple manner by customary methods for forming salts, for example by dissolving a compound of the general formula (I) in a suitable inert solvent and adding the acid, for example hydrochloric acid, and be isolated in a known manner, for example by filtration, and, if required, be purified by washing with an inert organic solvent.

Preferred for preparing metal salt complexes of the compounds of the general formula (I) are salts of metals of the II to IV main group and the I and II and the IV to VIII transition group of the Periodic System, examples which may be mentioned being copper, zinc, manganese, magnesium, tin, iron and nickel.

Suitable anions of the salts are those which are preferably derived from the following acids: hydrohalic acids, such as, for example, hydrochloric acid and hydrobromic acid, furthermore phosphoric acid, nitric acid and sulphuric acid.

The metal salt complexes of compounds of the general formula (I) can be obtained in a simple manner by customary processes, for example by dissolving the metal salt in alcohol, for example ethanol, and adding the solution to the compound of the general formula (I). Metal salt complexes can be isolated in a known manner, for example by filtration, and, if required, be purified by recrystallization.

The present invention furthermore relates to a composition for controlling unwanted microorganisms which comprises the active compounds according to the invention. These are preferably fungicidal compositions which comprise agriculturally suitable auxiliaries, solvents, carriers, surfactants or extenders.

Moreover, the invention relates to a method for controlling unwanted microorganisms, characterized in that the active compounds according to the invention are applied to the phytopathogenic fungi and/or their habitat.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Suitable liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

The compositions and formulations according to the invention generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds with at least one customary extender, solvent or diluent, emulsifier, dispersant, and/or binder or fixative, wetting agent, water repellent, if appropriate desiccants and UV stabilizers and, if appropriate, dyes and pigments, defoamers, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention furthermore relates to seed which has been treated in accordance with one of the methods described in the previous paragraph. The seeds according to the invention are used in methods for the protection of seed from undesirable microorganisms. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after planting or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants, from attack by phytopathogenic fungi, by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection agents. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture and viticulture. In particular, this takes the form of seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). The treatment of the seed of cereals (such as wheat, barley, rye, triticale and oats), maize and rice is of particular importance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating materials for seed, and also ULV formulations These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristyrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- und Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compounds or compositions according to the invention have a potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases permits the treatment of above-ground parts of plants, of propagation stock and seeds, and of the soil.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The active compounds according to the invention are suitable for the protection of plants and plant organs, for increasing the harvest yields, for improving the quality of the harvested crop, while being well tolerated by plants, having favourable toxicity to warm-blooded species and being environmentally friendly. They may be preferably employed as crop protection agents. They are active against normally sensitive and resistant species and against all or some stages of development.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rubaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, small radishes, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were to be expected: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the active compounds according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably to be treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:
1) Transgenic plants which synthesize a modified starch which is altered with respect to its chemo-physical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes,
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http:/gmoinfo.jrc.it/gmp_browse.aspx and http://www.agbios.com/dbase.php).

Moreover, in the protection of materials, the active compounds or compositions according to the invention can be employed for protecting industrial materials against attack and destruction by unwanted microorganisms, such as, for example, fungi and insects.

Furthermore, the compounds according to the invention can be used alone or in combinations with other active compounds as antifouling compositions.

Industrial materials in the present context are understood as meaning non-living materials which have been prepared for use in industry. For example, industrial materials which are intended to be protected by active compounds according to the invention from microbial change or destruction can be adhesives, sizes, paper, wallpaper, and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. The active compounds or compositions according to the invention may prevent disadvantageous effects, such as rotting, decay, discoloration, decoloration or formation of mould. Moreover, the compounds according to the invention can be employed for protecting objects which come into contact with saltwater or brackish water, in particular hulls, screens, nets, buildings, moorings and signaling systems, against fouling.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decoloration or formation of mould.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example, *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii*; *Typhula* species, such as, for example, *Typhula incarnata*; *Venturia* species, such as, for example, *Venturia inaequalis*;

root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example, *Rhizoctonia solani*; *Tapesia* species, such as, for example, *Tapesia acuformis*; *Thielaviopsis* species, such as, for example, *Thielaviopsis basicola*;

ear and panicle diseases (including corn cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as, for example, *Septoria nodorum*;

diseases caused by smut fungi, such as, for example, *Sphacelotheca* species, such as, for example, *Sphacelotheca reiliana*; *Tilletia* species, such as, for example, *Tilletia caries, T. controversa*; *Urocystis* species, such as, for example, *Urocystis occulta*; *Ustilago* species, such as, for example, *Ustilago nuda, U. nuda tritici*;

fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*; *Verticilium* species, such as, for example, *Verticilium alboatrum*;

seed- and soil-borne rot and wilt diseases, and also diseases of seedlings, caused, for example, by *Fusarium* species, such as, for example, *Fusarium culmorum*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*;

cancerous diseases, galls and witches' broom caused, for example, by *Nectria* species, such as, for example, *Nectria galligena*;

wilt diseases caused, for example, by *Monilinia* species, such as, for example, *Monilinia laxa*;

deformations of leaves, flowers and fruits caused, for example, by *Taphrina* species, such as, for example, *Taphrina deformans*;

degenerative diseases of woody plants caused, for example, by *Esca* species, such as, for example, *Phaeomoniella chlamydospora* and *Phaeoacremonium aleophilum* and *Fomitiporia mediterranea*;

diseases of flowers and seeds caused, for example, by *Botrytis* species, such as, for example, *Botrytis cinerea*;

diseases of plant tubers caused, for example, by *Rhizoctonia* species, such as, for example, *Rhizoctonia solani*; *Helminthosporium* species, such as, for example, *Helminthosporium solani*;

diseases caused by bacterial pathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

Fungal diseases on leaves, stems, pods and seeds caused, for example, by *alternaria* leaf spot (*Alternaria* spec. *atrans tenuissima*), anthracnose (*Colletotrichum gloeosporioides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or changing the industrial materials which may be mentioned are, for example, bacteria, fungi, yeasts, algae and slime organisms. The active compounds according to the invention preferably act against fungi, in particular moulds, wood-discoloring and wood-destroying fungi (Basidiomycetes), and against slime organisms and algae. Microorganisms of the following genera may be mentioned as examples: *Alternaria*, such as *Alternaria tenuis*; *Aspergillus*, such as *Aspergillus niger*, *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*, *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the active compounds according to the invention also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum*, *Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

Accordingly, the active compounds according to the invention can be used both in medical and in non-medical applications.

When using the active compounds according to the invention as fungicides, the application rates can be varied within a relatively wide range, depending on the kind of application. The application rate of the active compounds according to the invention is when treating plant parts, for example leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used);

when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;

when treating the soil: from 0.1 to 10 000 g/ha, preferably from 1 to 5000 g/ha.

These application rates are mentioned only by way of example and are not limiting in the sense of the invention.

The active compounds or compositions according to the invention can thus be employed for protecting plants for a certain period of time after treatment against attack by the pathogens mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be used as intermediates or precursors for the synthesis of other active compounds.

The active compounds according to the invention interfere with the metabolism of the plants and can therefore also be used as growth regulators.

Plant growth regulators may have various effects on plants. The effect of the compounds depends essentially on the time of application based on the development stage of the plant and also on the amounts of active compound applied to the plants or their environment and on the type of application. In each case, growth regulators should have a certain desired effect on the crop plants.

Plant growth-regulating compounds can be used, for example, for inhibiting the vegetative growth of the plants. Such an inhibition of growth is of economic interest, for example, in the case of grasses, as it is thus possible to reduce the frequency of mowing the grass in ornamental gardens, parks and sport facilities, on roadsides, at airports or in fruit cultures. Also of importance is the inhibition of the growth of herbaceous and woody plants on roadsides and in the vicinity of pipelines or overhead cables or quite generally in areas where strong plant growth is unwanted.

The use of growth regulators for inhibiting the longitudinal growth of cereal is also of importance. In this way, it is possible to reduce or eliminate completely the risk of lodging of the plants prior to the harvest. Moreover, in cereals growth regulators may strengthen the culm, which also acts against lodging. The application of growth regulators for stabilizing and strengthening culms permits the use of higher fertilizer application rates to increase the yield without any risk of lodging of cereals.

In many crop plants, inhibition of vegetative growth allows a more compact planting, and it is thus possible to achieve higher yields based on the soil surface. Another advantage of the smaller plants obtained in this manner is that the crops are easier to cultivate and harvest.

Inhibition of the vegetative plant growth may also lead to increased yields in that the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting the vegetative growth may also promote the generative growth in that more assimilates are formed, resulting in more or larger fruits.

In some cases, yield increases may be achieved by manipulating the metabolism of the plant, without any changes of vegetative growth being detectable. Furthermore, growth regulators may be used to change the composition of the plants, which in turn may result in an improved quality of the harvested products. Thus, it is possible, for example, to increase the sugar content in sugar beet, sugar cane, pineapples and also in citrus fruit, or to increase the protein content in soya beans or in cereals. It is also possible, for example, to inhibit, with growth regulators, the degradation of wanted ingredients, such as, for example, sugar in sugar beet or sugar cane, before or after harvest. Moreover, there can be a positive effect on the production or the elimination of secondary plant ingredients. An example which may be mentioned is the flow of latex in rubber trees.

Under the influence of growth regulators, parthenocarpic fruits may be formed. Furthermore, it may be possible to influence the sex of the flowers. It is also possible to produce sterile pollen, which is of great importance in breeding and producing hybrid seed.

By using growth regulators, branching of the plants can be controlled. On the one hand, by breaking the apical dominance, it is possible to promote the development of side shoots, which may be highly desirable in particular in the cultivation of ornamental plants also in combination with an inhibition of growth. However, on the other hand it is also possible to inhibit the growth of the side shoots. This effect is of particular interest for example in the cultivation of tobacco or in the cultivation of tomatoes.

The amount of leaf on the plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of the plants before they are transplanted.

Growth regulators can also be used to regulate fruit dehiscence. On the one hand, it is possible to prevent premature fruit dehiscence. On the other hand, it is also possible to promote fruit dehiscence or even flower abortion to achieve a desired mass ("thinning") to break alternation. Alternation is understood as the characteristic of some fruit species to deliver, owing to endogenous factors, highly varying yields from year to year. Finally, using growth regulators at the time of harvest, it is possible to reduce the forces required to detach the fruits to allow mechanical harvesting or to facilitate manual harvesting.

Growth regulators can furthermore be used to achieve faster or else delayed ripening of the harvested material before or after harvest. This is of particular advantage as this allows optimal adaptation to the requirements of the market. Furthermore, in some cases growth regulators may improve the fruit coloration. In addition, growth regulators can also be used to achieve maturation concentrated within a certain period of time. This allows complete mechanical or manual harvesting in a single operation, for example in the case of tobacco, tomatoes or coffee.

By using growth regulators, it is furthermore possible to influence the rest of seed or buds of the plants, so that plants such as, for example, pineapple or ornamental plants in nurseries, germinate, sprout or flower at a point in time when they are normally not inclined to do so. In areas where there is a risk of frost, it may be desirable to delay budding or germination of seeds with the aid of growth regulators to avoid damage owing to late frosts.

Finally, growth regulators may induce resistance of the plants to frost, drought or high salinity of the soil. This allows the cultivation of plants in regions which are normally unsuitable for this purpose.

The plants listed can be treated according to the invention in a particularly advantageous manner with the compounds of the general formula (I) and/or the compositions according to the invention. The preferred ranges stated above for the active compounds or compositions also apply to the treatment of these plants. Particular emphasis is given to the treatment of plants with the compounds or compositions specifically mentioned in the present text.

The invention is illustrated by the examples below. However, the invention is not limited to the examples.

PREPARATION EXAMPLES

Preparation of Compound No. 11 (Process C)

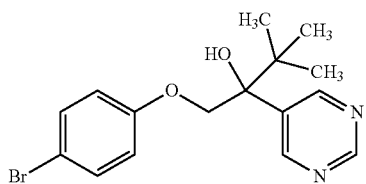 [SMILES: CC(C)(C)C(O)(COc1ccc(Br)cc1)c1cncnc1]

Under an atmosphere of argon, a mixture of 2.0 g (7.4 mmol) of 1-(4-bromophenoxy)-3,3-dimethylbutan-2-one and 1.35 g (8.5 mmol) of 5-bromopyrimidine in 20 ml of dry tetrahydrofuran is cooled to −120° C. n-Butyllithium (3.54 ml, 2.5 M, 8.9 mmol) is then added slowly with stirring. After the addition has ended, the reaction mixture is slowly warmed to room temperature overnight. 20 ml of a 10% strength ammonium chloride solution are added to the reaction mixture, and the organic phase is removed. The organic phase is then washed with 1 N hydrochloric acid and saturated aqueous sodium chloride solution, dried over sodium sulphate and filtered, and the filtrate is concentrated. The crude product is then purified by column chromatography (cyclohexane/ethyl acetate 1:1). This gives 1.89 g (73%) of the desired product.

Preparation of Compound No. 13 (Process B)

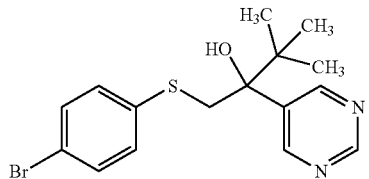 [SMILES: CC(C)(C)C(O)(CSc1ccc(Br)cc1)c1cncnc1]

At room temperature and under an atmosphere of argon, 0.19 g (60%, 4.9 mmol) of sodium hydride is added to 0.93 g (4.9 mmol) of 4-bromothiophenol dissolved in 25 ml of N,N-dimethylformamide, and the reaction mixture is stirred at room temperature for 1 h. 0.8 g (4.5 mmol) of 5-(2-tert-butyloxiran-2-yl)pyrimidine is then added, and the reaction mixture is stirred at 100° C. for 12 h. After cooling to room temperature, the solvent is removed under reduced pressure and saturated aqueous sodium chloride solution and ethyl acetate are added to the residue. The organic phase is separated off, dried over sodium sulphate, filtered and concentrated. The crude product is then purified by column chromatography (cyclohexane/ethyl acetate 1:1). This gives 0.50 g (29%) of the desired product.

Preparation of 5-(2-tert-butyloxiran-2-yl)pyrimidine

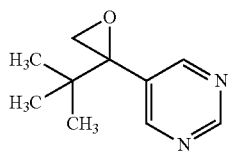

Under an atmosphere of argon, 10 ml of dimethyl sulphoxide are slowly added dropwise to 0.96 g (4.3 mmol) of trimethylsulphoxonium iodide and 0.17 g of sodium hydride (60%, 4.3 mmol). The reaction mixture is then stirred at room temperature for 15 min, and 0.65 g (3.9 mmol) of 2,2-dimethyl-1-(5-pyrimidinyl)-1-propanone, dissolved in 2 ml of tetrahydrofuran, is added. The reaction mixture is then stirred at 50° C. for 90 min. The reaction mixture is then concentrated under reduced pressure, and saturated aqueous sodium chloride solution and ethyl acetate are added to the residue. The organic phase is separated off dried over sodium sulphate, filtered and concentrated. This gives 0.70 g (99%) of the desired product, which is reacted without further purification.

Preparation of Compound No. 21 (Process B)

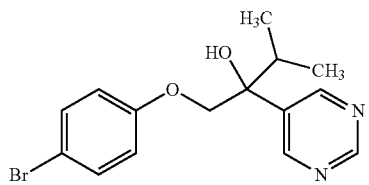 [SMILES: CC(C)C(O)(COc1ccc(Br)cc1)c1cncnc1]

At room temperature and under an atmosphere of argon, 78 mg (60%, 1.9 mmol) of sodium hydride are added to 0.34 g (1.9 mmol) of 4-bromophenol dissolved in 15 ml of N,N- dimethylformamide, and the reaction mixture is stirred at room temperature for 1 h. 0.29 g (1.8 mmol) of 5-(2-isopropyloxiran-2-yl)pyrimidine is then added, and the reaction mixture is stirred at 100° C. for 12 h. After cooling to room temperature, the solvent is removed under reduced pressure and saturated aqueous sodium chloride solution and ethyl acetate are added to the residue. The organic phase is separated off, dried over sodium sulphate, filtered and concentrated. The crude product is then purified by column chromatography (cyclohexane/ethyl acetate 1:1). This gives 82 mg (13%) of the desired product.

Preparation of
5-(2-isopropylpyloxiran-2-yl)pyrimidine

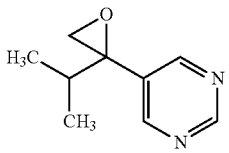

Under an atmosphere of argon, 50 ml of dimethyl sulphoxide are slowly added dropwise to 8.06 g (37 mmol) of trimethylsulphoxonium iodide and 1.47 g of sodium hydride (60%, 37 mmol). The reaction mixture is then stirred at room temperature for 15 min, and 5.00 g (33 mmol) of 2-methyl-1-(5-pyrimidinyl)-1-propanone, dissolved in 10 ml of tetrahydrofuran, are added. The reaction mixture is stirred at 50° C. for 90 min. The reaction mixture is then concentrated under reduced pressure, and saturated aqueous sodium chloride solution and ethyl acetate are added to the residue. The organic phase is separated off, dried over sodium sulphate, filtered and concentrated. This gives 1.36 g (25%) of the desired product, which is reacted without further purification.

Preparation of Compound No. 3 (Process B)

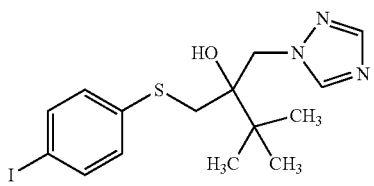 [SMILES: CC(C)(C)C(O)(CSc1ccc(I)cc1)Cn1cncn1]

At room temperature and under an atmosphere of argon, 68 mg (60%, 1.7 mmol) of sodium hydride are added to 0.40 g (1.7 mmol) of 4-iodothiophenol dissolved in 15 ml of N,N-dimethylformamide, and the reaction mixture is stirred at room temperature for 1 h. 028 g (1.5 mmol) of 1-[[2-(1,1-dimethylethyl)-2-oxiranyl]methyl]-1H-1,2,4-triazole (preparation see DE 3111238) is then added, and the reaction mixture is stirred at 100° C. for 12 h. After cooling to room temperature, the solvent is removed under reduced pressure and saturated aqueous sodium chloride solution and ethyl acetate are added to the residue. The organic phase is separated off, dried over sodium sulphate, filtered and concentrated. The crude product is then purified by column chromatography (cyclohexane/ethyl acetate 1:1). This gives 0.27 g (41%) of the desired product.

Analogously to the above examples and in accordance with the general descriptions of the processes according to the invention, it is possible to obtain the compounds of the formula (I) listed in Table 1 below.

TABLE 1

(I)

| No. | X | Y | Z | R | Physical data |
|---|---|---|---|---|---|
| 1 | 1H-1,2,4-triazol-1-ylmethyl | O | 4-I | $^tBu$ | $^1$H-NMR (400 MHz, DMSO-$d_6$): δ = 1.02 (s, 9H), 3.57 (d, J = 10 Hz, 1H), 3.88 (d, J = 10 Hz, 1H), 4.36 (d, J = 14 Hz, 1H), 4.56 (d, J = 14 Hz, 1H), 4.66 (s, 1H), 6.71 (m, 2H), 7.56 (m, 2H), 7.84 (s, 1H), 8.34 (s, 1H) ppm. |
| 2 | 1H-1,2,4-triazol-1-ylmethyl | S | 4-Br | $^tBu$ | |
| 3 | 1H-1,2,4-triazol-1-ylmethyl | S | 4-I | $^tBu$ | $^1$H-NMR (400 MHz, DMSO-$d_6$): δ = 0.96 (s, 9H), 3.11-3.21 (m, 2H), 4.38-4.41 (m, 2H), 4.72 (s, 1H), 7.06 (dd, J = 6 Hz, 2 Hz, 2H), 7.58 (dd, J = 6 Hz, 2 Hz, 2H), 7.89 (s, 1H), 8.42 (s, 1H) ppm. |
| 4 | 1H-1,2,4-triazol-1-ylmethyl | SO | 4-Br | $^tBu$ | |
| 5 | 1H-1,2,4-triazol-1-ylmethyl | SO | 4-I | $^tBu$ | |
| 6 | 1H-1,2,4-triazol-1-ylmethyl | $SO_2$ | 4-Br | $^tBu$ | |
| 7 | 1H-1,2,4-triazol-1-ylmethyl | $SO_2$ | 4-I | $^tBu$ | |
| 8 | 1H-1,2,4-triazol-1-ylmethyl | $CH_2$ | 4-I | $^tBu$ | |
| 9 | 1H-1,2,4-triazol-1-ylmethyl | O | 4-Br | 1-Me—cPr | $^1$H-NMR (400 MHz, DMSO-$d_6$): δ = −0.17 (m, 1H), 0.03 (m, 1H), 0.24 (m, 1H), 0.65 (m, 1H), 1.1 (s, 1H), 3.9 (d, 1H), 4.0 (d, 1H), 4.48 (dd, 2H), 4.9 (s, 1H), 6.9 (dd, 2H), 7.4 (dd, 2H), 7.9 (s, 1H), 8.4 (s, 1H) ppm. |
| 10 | 1H-1,2,4-triazol-1-ylmethyl | O | 4-I | 1-Me—cPr | $^1$H-NMR (400 MHz, DMSO-$d_6$): δ = −0.17 (m, 1H), 0.02 (m, 1H), 0.21 (m, 1H), 0.64 (m, 1H), 1.1 (s, 1H), 3.9 (d, 1H), 4.0 (d, 1H), 4.48 (dd, 2H), 4.9 (s, 1H), 6.8 (dd, 2H), 7.6 (dd, 2H), 7.9 (s, 1H), 8.4 (s, 1H) ppm. |

TABLE 1-continued (I)

| No. | X | Y | Z | R | Physical data |
|---|---|---|---|---|---|
| 11 | pyrimidin-5-yl | O | 4-Br | $^t$Bu | $^1$H-NMR (400 MHz, DMSO-$d_6$): δ = 0.93 (s, 9H), 4.22 (d, J = 10 Hz, 1H), 4.76 (d, J = 10 Hz, 1H), 5.32 (s, 1H), 6.89 (dd, J = 10 Hz, 2 Hz, 2H), 7.39 (dd, J = 10 Hz, 2 Hz, 2H), 8.80 (s, 2H), 9.01 (s, 1H) ppm. |
| 12 | pyrimidin-5-yl | O | 4-I | $^t$Bu | $^1$H-NMR (400 MHz, DMSO-$d_6$): δ = 0.91 (s, 9H), 4.20 (d, J = 10 Hz, 1H), 4.79 (d, J = 10 Hz, 1H), 5.50 (s, 1H), 6.77 (dd, J = 7 Hz, 2 Hz, 2H), 7.55 (dd, J = 7 Hz, 2 Hz, 2H), 8.80 (s, 2H), 9.03 (s, 1H) ppm. |
| 13 | pyrimidin-5-yl | S | 4-Br | $^t$Bu | $^1$H-NMR (400 MHz, DMSO-$d_6$): δ = 0.91 (s, 9H), 3.47 (d, J = 12 Hz, 1H), 4.05 (d, J = 12 Hz, 1H), 5.49 (s, 1H), 7.27 (m, 2H), 7.44 (m, 2H), 8.80 (s, 2H), 9.03 (s, 1H) ppm. |
| 14 | pyrimidin-5-yl | S | 4-I | $^t$Bu | |
| 15 | pyrimidin-5-yl | SO | 4-Br | $^t$Bu | |
| 16 | pyrimidin-5-yl | SO | 4-I | $^t$Bu | |
| 17 | pyrimidin-5-yl | SO$_2$ | 4-Br | $^t$Bu | |
| 18 | pyrimidin-5-yl | SO$_2$ | 4-I | $^t$Bu | |
| 19 | pyrimidin-5-yl | CH$_2$ | 4-Br | $^t$Bu | |
| 20 | pyrimidin-5-yl | CH$_2$ | 4-I | $^t$Bu | |
| 21 | pyrimidin-5-yl | O | 4-Br | $^i$Pr | $^1$H-NMR (400 MHz, DMSO-$d_6$): δ = 0.70 (d, J = 7 Hz, 3H), 0.93 (d, J = 7 Hz, 3H), 2.27 (sept, J = 7 Hz, 1H), 4.11 (d, J = 10 Hz, 1H), 4.36 (d, J = 10 Hz, 1H), 5.52 (s, 1H), 6.89 (dd, J = 7 Hz, 2 Hz, 2H), 7.41 (dd, J = 7 Hz, 2 Hz, 2H), 8.88 (s, 2H), 9.05 (s, 1H) ppm. |
| 22 | pyrimidin-5-yl | O | 4-I | $^i$Pr | $^1$H-NMR (400 MHz, DMSO-$d_6$): δ = 0.69 (d, J = 7 Hz, 3H), 0.93 (d, J = 7 Hz, 3H), 2.27 (sept, J = 7 Hz, 1H), 4.10 (d, J = 10 Hz, 1H), 4.34 (d, J = 10 Hz, 1H), 5.52 (s, 1H), 6.76 (dd, J = 9 Hz, 3 Hz, 2H), 7.55 (dd, J = 9 Hz, 3 Hz, 2H), 8.88 (s, 2H), 9.05 (s, 1H) ppm. |
| 23 | pyrimidin-5-yl | O | 4-Br | 1-F—cPr | $^1$H-NMR (400 MHz, DMSO-$d_6$): δ = 0.9-1.25 (m, 4H), 4.35 (s, 1H), 4.41 (dd, J = 10 Hz, 2 Hz, 1H), 4.54 (dd, J = 10 Hz, 2 Hz, 1H), 6.90 (dd, J = 7 Hz, 2 Hz, 2H), 7.43 (dd, J = 7 Hz, 2 Hz, 2H), 8.95 (s, 2H), 9.11 (s, 1H) ppm. |
| 24 | pyridin-3-yl | O | 4-I | $^t$Bu | |
| 25 | pyridin-3-yl | S | 4-I | $^t$Bu | |
| 26 | pyridin-3-yl | SO | 4-Br | $^t$Bu | |
| 27 | pyridin-3-yl | SO | 4-I | $^t$Bu | |
| 28 | pyridin-3-yl | SO$_2$ | 4-Br | $^t$Bu | |
| 29 | pyridin-3-yl | SO$_2$ | 4-I | $^t$Bu | |
| 30 | pyridin-3-yl | CH$_2$ | 4-Br | $^t$Bu | $^1$H-NMR (400 MHz, DMSO-$d_6$): δ = 0.84 (s, 9H), 1.91-2.00 (m, 2H), 2.45-2.58 (m, 2H), 4.92 (s, 1H), 7.16 (d, J = 8 Hz, 2H), 7.37 (bs, 1H), 7.44 (d, J = 8 Hz, 2H), 7.83 (d, 1H), 8.73 (bs, 1H), 8.68 (bs, 1H) ppm |
| 31 | pyridin-3-yl | O | 4-I | $^t$Bu | |
| 32 | pyridin-3-yl | O | 4-Br | 1-F—cPr | $^1$H-NMR (400 MHz, DMSO-$d_6$): δ = 0.75-1.25 (m, 4H), 4.21 (s, 1H), 4.41 (dd, J = 10 Hz, 2 Hz, 1H), 4.51 (dd, J = 10 Hz, 2 Hz, 1H), 6.90 (d, J = 9 Hz, 2H), 7.36 (dd, 1H), 7.42 (d, J = 9 Hz, 2H), 7.96 (dd, 1H), 8.52 (dd, 1H), 8.80 (s, 1H) ppm. |
| 33 | pyrimidin-5-yl | O | 3-Br | $^t$Bu | 1H-NMR (400 MHz, DMSO-d6): δ = 0.91 (s, 9H), 4.22 (d, J = 10 Hz, 1H), 4.86 (d, J = 10 Hz, 1H), 5.50 (s, 1H), 6.90 (m, 1H), 7.11 (m, 1H), 7.21 (m, 2H), 8.21 (s, 2H), 9.04 (s, 1H) ppm. |
| 34 | pyrimidin-5-yl | O | 3-I | $^i$Pr | 1H-NMR (400 MHz, DMSO-d6): δ = 0.70 (d, J = 7 Hz, 3H), 0.93 (d, J = 7 Hz, 3H), 2.26 (m, 1H), 4.12 (d, J = 10 Hz, 1H), 4.37 (d, J = 10 Hz, 1H), 5.51 (s, 1H), 6.92 (m, 1H), 7.04 (m, 1H), 7.30 (m, 2H), 8.88 (s, 2H), 9.06 (s, 1H) ppm. |

TABLE 1-continued (I)

| No. | X | Y | Z | R | Physical data |
|---|---|---|---|---|---|
| 35 | pyrimidin-5-yl | O | 3-Br | 1-F—cPr | $^1$H-NMR (600 MHz, DMSO-d$_6$): δ = 0.82-1.25 (m, 4H), 4.43 (d, J = 10 Hz, 1H), 4.53 (s, 1H, OH), 4.55 (d, J = 10 Hz, 1H), 6.93 (dd, J = 8 Hz, 2 Hz, 1H), 6.90 (dd, J = 7 Hz, 2 Hz, 2H), 7.13-7.22 (m, 3H), 8.96 (s, 2H), 9.11 (s, 1H) ppm. |
| 36 | pyridin-3-yl | O | 3-Br | 1-F—cPr | 1H-NMR (600 MHz, DMSO-d6): δ = 0.80-1.22 (m, 4H), 4.18 (s, 1H), 4.43 (d, J = 10 Hz, 1H), 4.52 (d, J = 10 Hz, 1H), 6.94 (dd, J = 8 Hz, J = 8 Hz, 2H), 7.13-7.23 (m, 3H), 7.36 (dd, J = 8 Hz, 4.5 Hz, 1H), 7.96 (d, J = 8 Hz, 1H), 8.53 (dd, J = 5 Hz, 1.3 Hz, 1H), 8.80 (s, 1H) ppm. |
| 37 | pyrimidin-5-yl | O | 4-I | 1-F—cPr | $^1$H-NMR (600 MHz, DMSO-d$_6$): δ = 0.81-1.26 (m, 4H), 4.40 (s, 1H, OH), 4.41 (d, J = 8 Hz, 1H), 4.53 (d, J = 8 Hz, 1H), 6.89 (d, J = 9 Hz, 2H), 7.42 (d, J = 9 Hz, 2H), 8.95 (s, 2H), 9.10 (s, 1H) ppm. |
| 38 | 1H-1,2,4-triazol-1-ylmethyl | O | 3-Br | $^t$Bu | $^1$H-NMR (400 MHz DMSO-d$_6$): δ = 1.02 (s, 9H), 3.57 (d, 1H), 3.88 (d, 1H), 4.36 (d, 1H), 4.56 (d, 1H), 4.9 (s, 1H), 6.85 (dd, 1H), 7.05 (brs, 1H), 7.15 (d, 1H), 7.25 (t, 1H), 7.9 (s, 1H), 8.4 (s 1H), ppm. |
| 39 | 1H-1,2,4-triazol-1-ylmethyl | O | 3-Br | 1-Me—cPr | $^1$H-NMR (400 MHz, DMSO-d$_6$): δ = −0.2 to −0.14 (m, 1H), 0.01-0.04 (m, 1H), 0.22-0.25 (m, 1H), 0.6-0.65 (m, 1H) 1.1 (s, 3H), 3.9 (d, 1H), 4.1 (d, 1H), 4.45 (ABq, 2H), 4.9 (s, 1H), 6.95 (dd, 1H), 7.0-7.2 (m, 2H), 7.25 (t, 1H), 7.9 (s, 1H) 8.4 (s 1H) ppm. |
| 40 | 1H-1,2,4-triazol-1-ylmethyl | O | 3-I | $^t$Bu | $^1$H-NMR (400 MHz, DMSO-d$_6$): δ = 1.02 (s, 9H), 3.55 (d, 1H), 3.9 (d, 1H), 4.4 (d, 1H), 4.6 (d, 1H), 4.8 (brs, 1H), 6.9 (dd, 1H), 7.1 (t, 1H), 7.2 (brs, 1H), 7.3 (d, 1H), 7.9 (s, 1H), 8.4 (s 1H), ppm. |
| 41 | 1H-1,2,4-triazol-1-ylmethyl | O | 3-I | 1-Me—cPr | $^1$H-NMR (400 MHz, DMSO-d$_6$): δ = −0.2 to −0.14 (m, 1H), 0.01-0.04 (m, 1H), 0.22-0.25 (m, 1H), 0.6-0.65 (m, 1H) 1.1 (s, 3H), 3.9 (d, 1H), 4.05 (d, 1H), 4.45 (ABq, 2H), 4.9 (s, 1H), 7.0 (dd, 1H), 7.1 (t, 1H), 7.25-7.35 (m, 2H), 7.9 (s, 1H) 8.4 (s, 1H) ppm. |
| 42 | 1H-1,2,4-triazol-1-ylmethyl | O | 2-Br | 1-Me—cPr | $^1$H-NMR (400 MHz, DMSO-d$_6$): δ = −0.2 to −0.14 (m, 1H), 0.01-0.04 (m, 1H), 0.290.35 (m, 1H), 0.68-0.75 (m, 1H) 1.2 (s, 3H), 3.95 (d, 1H), 4.05 (d, 1H), 4.55 (ABq, 2H), 6.9 (t, 1H), 7.1 (d, 1H), 7.35 (t, 1H), 7.6 (d, 1H), 7.9 (s, 1H) 8.4 (s, 1H) ppm. |
| 43 | 1H-1,2,4-triazol-1-ylmethyl | O | 2-I | $^t$Bu | $^1$H-NMR (400 MHz, DMSO-d$_6$): δ = 1.1 (s, 9H), 3.5 (d, 1H), 4.0 (d, 1H), 4.45 (d, 1H), 4.75 (d, 1H), 4.8 (brs, 1H), 6.8 (t, 1H), 6.9 (d, 1H), 7.45 (t, 1H), 7.8 (d, 1H), 7.95 (s, 1H), 8.35 (s 1H), ppm. |
| 44 | 1H-1,2,4-triazol-1-ylmethyl | O | 2-I | 1-Me—cPr | $^1$H-NMR (400 MHz, DMSO-d$_6$): δ = −0.2 to −0.14 (m, 1H), 0.01-0.04 (m, 1H), 0.29-0.32 (m, 1H), 0.71-0.75 (m, 1H) 1.2 (s, 3H), 3.95 (d, 1H), 4.05 (d, 1H), 4.55 (d, 1H), 4.65 (d, 1H), 4.9 (s, 1H), 6.7-6.9 (m, 1H), 7.0 (d, 1H), 7.3-7.4 (m, 1H), 7.8 (d, 1H) 7.9 (s 1H), 8.4 (s, 1H) ppm. |
| 45 | 1H-1,2,4-triazol-1-ylmethyl | O | 2-Br | $^t$Bu | $^1$H-NMR (400 MHz, DMSO-d$_6$): δ = 1.1 (s, 9H), 3.5 (d, 1H), 3.95 (d, 1H), 4.45 (d, 1H), 4.65 (d, 1H), 4.8 (s, 1H), 6.9 (t, 1H), 6.95 (d, 1H), 7.3 (t, 1H), 7.6 (d, 1H), 7.85 (s, 1H), 8.4 (s, 1H), ppm. |
| 46 | 1H-1,2,4-triazol-1-ylmethyl | S | 3-Br | $^t$Bu | $^1$H-NMR (400 MHz, DMS0-d$_6$): δ = 0.95 (s, 9H), 4.4 (ABq, 2H), 4.95 (brs, 1H), 7.2-7.35 (m, 3H), 7.5 (brs, 1H), 7.95 (s, 1H), 8.5 (s 1H), ppm. One CH$_2$ group is at 3.3 ppm under the DMSO peak.. |

TABLE 1-continued $$\text{(I)}$$

Structure: Z-(phenyl ring)-Y-CH(R)-C(OH)(X)- with substituent positions

| No. | X | Y | Z | R | Physical data |
|---|---|---|---|---|---|
| 47 | 1H-1,2,4-triazol-1-ylmethyl | S | 2-Br | $^t$Bu | $^1$H-NMR (400 MHz, DMSO-$d_6$): δ = 1.0 (s, 9H), 4.45 (ABq, 2H), 5.0 (brs, 1H), 7.1 (t, 1H), 7.25-7.35 (m, 2H), 7.6 (d, 1H), 7.9 (s 1H), 8.5 (s 1H), ppm. One CH$_2$ group is at 3.3 ppm under the DMSO peak.. |
| 48 | 1H-1,2,4-triazol-1-ylmethyl | S | 3-Br | 1-Me—cPr | $^1$H-NMR (400 MHz, DMSO-$d_6$): δ = −0.2 to −0.16 (m, 1H), 0.01-0.05 (m, 1H), 0.15-0.18 (m, 1H), 0.71-0.75 (m, 1H) 1.1 (s, 3H), 3.2 (d, 1H), 3.45 (d, 1H), 4.45 (ABq, 2H), 4.9 (s, 1H), 7.25 (dd, 1H), 7.3-7.4 (m, 2H), 7.5 (s, 1H) 7.95 (s 1H), 8.4 (s, 1H) ppm. |
| 49 | 1H-1,2,4-triazol-1-ylmethyl | S | 2-Br | 1-Me—cPr | $^1$H-NMR (400 MHz, DMSO-$d_6$): δ = −0.2 to −0.16 (m, 1H), 0.01-0.05 (m, 1H), 0.15-0.18 (m, 1H), 0.73-0.8 (m, 1H) 1.1 (s, 3H), 3.15 (d, 1H), 3.4 (d, 1H), 4.4 (ABq, 2H), 5.0 (s, 1H), 7.0-7.15 (m, 1H), 7.3-7.4 (m, 2H), 7.6 (d, 1H) 7.95 (s 1H), 8.45 (s, 1H) ppm. |
| 50 | 1H-1,2,4-triazol-1-ylmethyl | S | 2-Br | 1-Cl—cPr | $^1$H-HMR (400 MHz, DMSO-$d_6$): δ = 0.60-0.7 (m, 2H), 0.85-0.92 (m, 1H), 1.2-1.35 (m, 1H) 3.35 (d, 1H), 3.6 (d, 1H), 4.60 (ABq, 2H), 5.7 (s, 1H), 7.0-7.17 (m, 1H), 7.3-7.41 (m, 2H), 7.6 (d, 1H) 7.95 (s 1H), 8.45 (s, 1H) ppm. |
| 51 | 1H-1,2,4-triazol-1-ylmethyl | S | 3-Br | 1-Cl—cPr | $^1$H-NMR (400 MHz, DMSO-$d_6$): δ = 0.60-0.7 (m, 2H), 0.83-0.91 (m, 1H), 1.2-1.33 (m, 1H) 3.39 (d, 1H), 3.65 (d, 1H), 4.55 (ABq, 2H), 5.65 (s, 1H), 7.25 (t, 1H), 7.33-7.43 (m, 2H), 7.55 (s, 1H) 8.0 (s 1H), 8.4 (s, 1H) ppm. |

USE EXAMPLES

Example A

*Sphaerotheca* Test (Cucumber)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young cucumber plants are sprayed with the preparation of active compound at the stated application rate. 1 day after the treatment, the plants are inoculated with a spore suspension of *Sphaerotheca fuliginea*. The plants are then placed in a greenhouse at a relative atmospheric humidity of 70% and a temperature of 23° C. Evaluation is carried out 7 days after the inoculation. 0% means an efficacy which corresponds to that of the control, whereas an efficacy of 100% means that no infection is observed.

In this test, the following compounds according to the invention 1, 2, 3, 4, 9, 10, 11, 12, 13, 21, 22, 23, 30, 32, 33, 35, 36 and 37 show, at an active compound concentration of 500 ppm, an efficacy of 70% or more.

Example B

*Leptosphaeria nodorum* Test (Wheat)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young wheat plants are sprayed with the preparation of active compound at the stated application rate. 1 day after the treatment, the plants are inoculated with an aqueous spore suspension of *Leptosphaeria nodorum* and then remain at 100% relative atmospheric humidity and 22° C. for 48 h. The plants are then placed in a greenhouse at 90% relative atmospheric humidity and a temperature of 22° C. Evaluation is carried out 7-9 days after the inoculation. 0% means an efficacy which corresponds to that of the control, whereas an efficacy of 100% means that no infection is observed.

In this test, the following compounds according to the invention 1, 2, 3, 10, 11, 12, 13, 21, 22, 23, 30, 32, 33, 35, 36 and 37 show, at an active compound concentration of 500 ppm, an efficacy of 70% or more.

Example C

*Alternaria* Test (Tomato)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are inoculated with an aqueous spore suspension of *Alternaria solani*. The plants are then placed in an incubation cabin at about 20° C. and 100% relative atmospheric humidity. Evaluation is carried out 3 days after the inoculation. 0% means an efficacy which corresponds to that of the control, whereas an efficacy of 100% means that no infection is observed.

Results: *Alternaria* Test (Tomato)/Protective

Example D

*Pyrenophora teres* Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for

| Active compounds | Active compound application rate in ppm | Efficacy in % |
|---|---|---|
| known from EP-A 0 040 345, Example I-1: | 100 | 45 |
| known from EP-A 0 028 755, Example 1: | 100 | 75 |
| according to the invention, Example 1: | 100 | 94 |
| according to the invention, Example 11: | 100 | 99 |

Furthermore, in this test, the following compounds according to the invention 2, 3, 10, 9, 23, 22, 12, 33 and 37 show, at an active compound concentration of 100 ppm, an efficacy of 70% or more.

protective activity, young plants are sprayed with the preparation of active compound at the stated application rate. After the spray coating has dried on, the plants are sprayed with a spore suspension of *Pyrenophora teres*. The plants remain in an incubation cabin at 20° C. and a relative atmospheric humidity of 100% for 48 hours. The plants are placed in a greenhouse at a temperature of about 20° C. and a relative atmospheric humidity of about 80%. Evaluation is carried out 8 days after the inoculation. 0% means an efficacy which corresponds to that of the control, whereas an efficacy of 100% means that no infection is observed.

Results: *Pyrenophora teres* Test (Barley)/Protective an aqueous conidia suspension of the apple scab pathogen *Venturia inaequalis* and then remain in an incubation cabin at about 20° C. and 100% relative atmospheric humidity for 1 day. The plants are then placed in a greenhouse at about 21° C. and a relative atmospheric humidity of about 90%. Evaluation is carried out 10 days after the inoculation. 0% means an efficacy which corresponds to that of the control, whereas an efficacy of 100% means that no infection is observed.

| Active compounds | Active compound application rate in ppm | Efficacy in % |
|---|---|---|
| known from EP-A 0 40 345, Example I-1: | 1000 | 57 |
| known from EP-A 0 028 755, Example 1: | 500 | 93 |
| according to the invention, Example 1: | 1000 | 86 |
| according to the invention, Example 11: | 500 | 100 |

Example E

*Venturia* Test (Apple)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are inoculated with In this test, the following compounds according to the invention 1, 2, 3, 9, 10, 11, 12, 22, 23 and 37 show, at an active compound concentration of 100 ppm, an efficacy of 70% or more.

Example F

*Blumeria graminis* Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are dusted with spores of *Blumeria graminis* f.sp. *hordei*. The plants are placed in a greenhouse at a temperature of about 18° C. and a relative atmospheric humidity of about 80% to promote the development of mildew pustules. Evaluation is carried out 7 days after the inoculation. 0% means an efficacy which corresponds to that of the control, whereas an efficacy of 100% means that no infection is observed.

In this test, the following compounds according to the invention 1, 2, 3, 9, 10, 11, 12, 22 and 33 show, at an active compound concentration of 500 ppm, an efficacy of 70% or more.

Example G

*Puccinia triticina* Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with a spore suspension of *Puccinia triticina*. The plants remain in an incubation cabin at 20° C. and a relative atmospheric humidity of 100/for 48 hours. The plants are placed in a greenhouse at a temperature of about 20° C. and a relative atmospheric humidity of about 80%. Evaluation is carried out 8 days after the inoculation. 0% means an efficacy which corresponds to that of the control, whereas an efficacy of 100% means that no infection is observed.

In this test, the following compounds according to the invention 1, 2, 3, 9, 10, 11, 12 and 22 show, at an active compound concentration of 1000 ppm, an efficacy of 70% or more.

Example H

Production of Fumonisin FB1 by *Fusarium proliferatum*

The compounds were tested in microtitre plates in a fumonisin-inducing liquid medium (0.5 g of malt extract, 1 g of yeast extract, 1 g of bactopeptone, 20 g of fructose, 1 g of $KH_2PO_4$, 0.3 g of $MgSO_4 \times 7H_2O$, 0.3 g of KCl, 0.05 g of $ZnSO_4 \times 7H_2O$ and 0.01 g of $CuSO_4 \times 5H_2O$ per liter) with DMSO (0.5%). Inoculation was carried out using a concentrated spore suspension of *Fusarium proliferatum* at a final concentration of 2000 spores/ml. The plate was incubated at 20° C. and high atmospheric humidity for 5 days. At the beginning and after 5 days, the OD was measured at OD620 (repeated measurements: 3×3 measurements per well) to calculate the inhibition of growth. After 5 days, a sample of the liquid medium was removed and diluted 1:1000 with 50% strength acetonitrile. The concentration of FB1 of the diluted samples was analyzed by HPLC-MS/MS, and the measured values were used to calculate the inhibition of fumonisin FB1 production compared to an active compound-free control.

HPLC-MS/MS was carried out using the following parameters:
ionization: ESI positive
ion spray voltage: 5500 V
spray gas temperature: 500° C.
decluster potential: 114 V
collision energy: 51 eV
collision gas: $N_2$
NMR trace: 722.3>352.3; dwell time 100 ms
HPLC column: Waters Atlantis T3 (trifunctionally C18-bonded, sealed)
particle size: 3 µm
column dimensions: 50×2 mm
temperature: 40° C.
solvent A: water+0.1% HCOOH (v/v)
solvent B: acetonitrile+0.1% HCOOH (v/v)
flow rate 400 µl/minute
injection volume: 5 µl
gradient:

| Time [min] | A % | B % |
|---|---|---|
| 0 | 90 | 10 |
| 2 | 5 | 95 |
| 4 | 5 | 95 |
| 4.1 | 90 | 10 |
| 9 | 90 | 10 |

Examples of the Inhibition of Fumonisin FB1 Production

Examples Nos. 1, 3, 9, 10, 11, 12, 13, 21, 22, 23 and 32 showed an activity of >80% for the inhibition of fumonisin FB1 production at a concentration of 50 µM. The inhibition of growth of *Fusarium proliferatum* of the examples mentioned varied from 36 to 100% at 50 µM.

Example I

Production of DON/Acetyl-DON by *Fusarium graminearum*

The compounds were tested in microtitre plates in a DON-inducing liquid medium (1 g of $(NH_4)_2HPO_4$, 0.2 g of $MgSO_4 \times 7H_2O$, 3 g of $KH_2PO_4$, 10 g of glycerol, 5 g of NaCl and 40 g of sucrose per liter) and DMSO (0.5%). Inoculation was carried out using a concentrated spore suspension of *Fusarium graminearum* at a final concentration of 2000 spores/ml. The plate was incubated at 28° C. and high atmospheric humidity for 7 days. At the beginning and after 3 days, the OD was measured at OD620 (repeated measurements: 3×3 measurements per well) to calculate the inhibition of growth. After 7 days, 1 volume of an 84/16 acetonitrile/water mixture was added, and a sample of the liquid medium from each well was then removed and diluted 1:100 in 10% strength acetonitrile. The proportions of DON and acetyl-DON of the samples were analyzed by HPLC-MS/MS, and the measured values were used to calculate the inhibition of DON/AcDON production compared to an active compound-free control.

HPLC-MS/MS measurements were carried out using the following parameters:
ionization: ESI negative
ion spray voltage: −4500 V
spray gas temperature: 500° C.
decluster potential: −40 V
collision energy: −22 eV
collision gas: $N_2$
NMR trace: 355.0>264.9
HPLC column: Waters Atlantis T3 (trifunctionally C18-bonded, sealed)
particle size: 3 µm column dimensions: 50×2 mm
temperature: 40° C.
solvent A: water/2.5 mM NH$_4$OAc+0.05% CH$_3$COOH (v/v)
solvent B: methanol/2.5 mM NH$_4$OAc+0.05% CH$_3$COOH (v/v)
flow rate: 400 μl/minute
injection volume: 11 μl
gradient:

| Time [min] | A % | B % |
|---|---|---|
| 0 | 100 | 0 |
| 0.75 | 100 | 0 |
| 1.5 | 5 | 95 |
| 4 | 5 | 95 |
| 5 | 100 | 0 |
| 10 | 100 | 0 |

Examples of DON Inhibition

Examples Nos. 1, 3, 9, 10, 11, 12, 21, 22 and 32 showed an activity of >80% for the inhibition of DON/AcDON production at 50 μM. The inhibition of growth of *Fusarium graminearum* of the examples mentioned varied from 34 to 99% at 50 μM.

Example J

Production of Aflatoxins by *Aspergillus parasiticus*

The compounds were tested in microtitre plates (black 96-well plates with flat and transparent bottom) in an aflatoxin-inducing liquid medium (20 g of sucrose, 4 g of yeast extract, 1 g of KH$_2$PO$_4$ and 0.5 g of MgSO$_4$×7H$_2$O per liter), with 20 mM Cavasol (hydroxypropyl-beta-cyclodextrin) and 1% DMSO added. Inoculation was carried out using a concentrated spore suspension of *Aspergillus* parasiticus at a final concentration of 1000 spores/ml. The plate was incubated at 20° C. and high atmospheric humidity for 7 days. After 7 days, the OD was measured at OD620 (repeated measurements: 4×4 measurements per well) to calculate the inhibition of growth. At the same time, across the bottom of the plate the fluorescence was measured at Em$_{360nm}$ and Ex$_{426nm}$ (repeated measurements: 3×3 measurements per well) to calculate the inhibition of aflatoxin production compared to an active compound-free control.

Examples of an Inhibition of Aflatoxin Production

Examples Nos. 11 and 32 showed, at 50 μM, an activity of >80% inhibition of aflatoxin production. The inhibition of the growth of *Aspergillus parasiticus* at 50 μM by these examples varied in the range from 43 to 69%.

Example K

Phytoregulatory Pre- and Post-Emergence Action

Phytoregulatory Pre-Emergence Action

Seeds of monocotyledonous or dicotyledonous crop plants are placed in wood-fibre pots in sandy loam and covered with soil. The test compounds, formulated in the form of wettable powders (WP), are then, as an aqueous suspension with a water application rate of 600 l/ha (converted), with 0.2% of wetting agent added, applied at various dosages to the surface of the covering soil. After the treatment, the pots are placed in a greenhouse and kept under good growth conditions for the test plants. The visual assessment of the suppression of growth in the test plants is carried out after a trial period of about 3 weeks by comparison with untreated controls (phytoregulatory activity in percent: 100% activity=maximum inhibition of plant growth, 0% activity=plant growth like that of an untreated control.)

Phytoregulatory Post-Emergence Action

Seeds of monocotyledonous and dicotyledonous crop plants are placed in sandy loam in wood-fibre pots, covered with soil and cultivated in a greenhouse under good growth conditions. 2 to 3 weeks after sowing, the test plants are treated at the one-leaf stage. The test compounds, formulated as wettable powders (WP), are, with a water application rate of 600l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (phytoregulatory activity in percent: 100% activity=maximum inhibition of plant growth, 0% activity=plant growth like that of an untreated control.)

Results: Phytoregulatory Pre- and Post-Emergence Action

| | Post-emergence dosage | Inhibition of the growth of useful or harmful plants in % | | |
|---|---|---|---|---|
| Active compounds | [g of a.i./ha] | SETVI | TRZAS | BRSNW |
| known from EP-A 0 028 755, Example 1: | 80 | 50 | 50 | 60 |

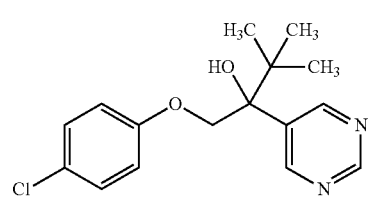 [SMILES: CC(C)(C)C(O)(COc1ccc(Cl)cc1)c1cncnc1]

-continued

| Active compounds | Post-emergence dosage [g of a.i./ha] | Inhibition of the growth of useful or harmful plants in % | | |
|---|---|---|---|---|
| | | SETVI | TRZAS | BRSNW |
| according to the invention, Example 11: | 80 | 70 | 70 | 60 |

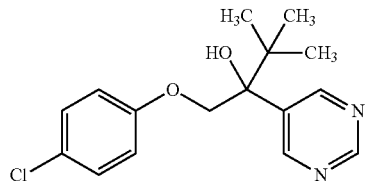 [SMILES: CC(C)(C)C(O)(COc1ccc(Cl)cc1)c1cncnc1]

SETVI = *Setaria viridis* (green foxtail),
TRZAS = *Triticum aestivum* (common wheat),
BRSNW = *Brassica napus* (rape).

| Active compounds | Pre-emergence dosage [g of a.i./ha] | Inhibition of the growth of useful or harmful plants in % | |
|---|---|---|---|
| | | ORYSA | BRSNW |
| known from EP-A 0 028 755, Example 1: | 80 | 40 | 70 |

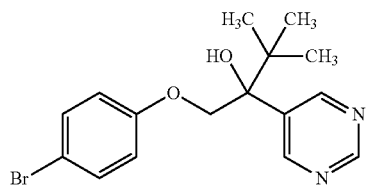 [SMILES: CC(C)(C)C(O)(COc1ccc(Cl)cc1)c1cncnc1]

| | | | |
|---|---|---|---|
| according to the invention, Example 11: | 80 | 60 | 80 |

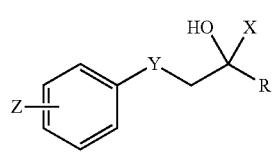

BRSNW = *Brassica napus* (rape),
ORYSA = *Oryza sativa* (rice).

The invention claimed is:

1. A compound of formula (I)

$$\text{(I)}$$

in which:
X represents 3-pyridinyl,
Y represents $CH_2$,
Z represents bromine or iodine,
R represents tert-butyl, isopropyl, 1-halocyclopropyl, 1-($C_1$-$C_4$-alkyl)cyclopropyl, 1-($C_1$-$C_4$-alkoxy)cyclopropyl or 1-($C_1$-$C_4$-alkylthio)cyclopropyl, and the agrochemically active salts thereof.

2. The compound of formula (I) according to claim 1 in which:
X represents 3-pyridinyl
Y represents $CH_2$,
Z represents bromine which is located in position 4, and
R represents tert-butyl.

3. A composition for controlling phytopathogenic harmful fungi, comprising at least one compound of formula (I) according to claim 1 and an extender, a surfactant, or a combination thereof.

4. A process for preparing a composition for controlling phytopathogenic harmful fungi, comprising mixing a compound of formula (I) according to claim 1 with an extender, a surfactant, or a combination thereof.

5. A process for preparing a compound of formula (I) according to claim 1 comprising:

compound of formula (VI)

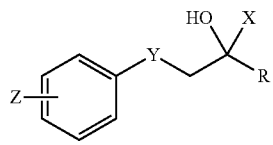

in which Y, Z and R have the meanings given in claim 1, is reacted with a halide of formula (VII)

Hal-X³                     (VII)

in which Hal represents halogen, and $X^3$ is 3-pyridinyl, in the presence of a diluent and in the presence of an organic alkali metal compound.

6. A method for controlling phytopathogenic harmful fungi, comprising applying a compound of formula (I) according to claim 1 to the phytopathogenic harmful fungi, their habitat or a combination thereof.

* * * * *

UNITED STATES PATENT AND TRADEMARK OFFICE
CERTIFICATE OF CORRECTION

PATENT NO. : 9,321,732 B2
APPLICATION NO. : 14/458867
DATED : April 26, 2016
INVENTOR(S) : Nising et al.

Page 1 of 1

It is certified that error appears in the above-identified patent and that said Letters Patent is hereby corrected as shown below:

Claims

Column 53

Lines 2-9, claim 5, please replace

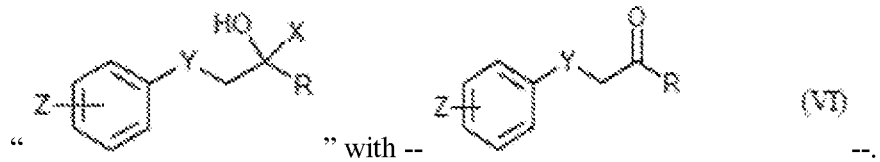

" with --   --.

Signed and Sealed this
Twenty-sixth Day of July, 2016

Michelle K. Lee
*Director of the United States Patent and Trademark Office*